(12) United States Patent
Silbert

(10) Patent No.: US 12,320,818 B2
(45) Date of Patent: Jun. 3, 2025

(54) METHOD OF PROCESSING A SAMPLE

(71) Applicant: GEN-PROBE INCORPORATED, San Diego, CA (US)

(72) Inventor: Rolf Silbert, Del Mar, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 206 days.

(21) Appl. No.: 16/499,814

(22) PCT Filed: Mar. 30, 2018

(86) PCT No.: PCT/US2018/025463
§ 371 (c)(1),
(2) Date: Sep. 30, 2019

(87) PCT Pub. No.: WO2018/183890
PCT Pub. Date: Oct. 4, 2018

(65) Prior Publication Data
US 2020/0103430 A1 Apr. 2, 2020

Related U.S. Application Data

(60) Provisional application No. 62/479,797, filed on Mar. 31, 2017.

(51) Int. Cl.
*G16H 10/40* (2018.01)
*G01N 35/00* (2006.01)
*G16H 10/65* (2018.01)

(52) U.S. Cl.
CPC ....... *G01N 35/00732* (2013.01); *G16H 10/65* (2018.01); *G01N 2035/00752* (2013.01);
(Continued)

(58) Field of Classification Search
CPC .................... G01N 35/00732–35/02
See application file for complete search history.

(56) References Cited

U.S. PATENT DOCUMENTS 4,338,279 A * 7/1982 Orimo ................. G01N 21/253
422/65
2010/0288061 A1* 11/2010 Hagen ................ G01N 35/1004
73/864.91
(Continued)

FOREIGN PATENT DOCUMENTS

EP 2 230 520 A1 9/2010
WO 2006/130760 A2 12/2006
(Continued)

OTHER PUBLICATIONS

International Search Report and Written Opinion of the International Searching Authority directed to related International Patent Application No. PCT/US2018/025463, mailed Oct. 4, 2018; 11 pages.

(Continued)

*Primary Examiner* — Paul S Hyun
(74) *Attorney, Agent, or Firm* — Sterne, Kessler, Goldstein & Fox P.L.L.C.; Charles B. Cappellari

(57) ABSTRACT

A sample receptacle can be used for ordering assays to be performed by an automatic sample processing instrument. The sample receptacle can include a body defining a chamber for containing a sample and a label. The label can include discrete areas configured to be altered from a first assay order state to a second assay order state. Each discrete area has a known association with a different assay. The label can also include assay-identifying indicia indicating the respective assay associated with a respective discrete area. A method of processing a sample in a receptacle having one or more assay order states can include automatically determining assay order states of the discrete areas and performing an assay on the sample, using the automatic sample processing instruments, based on the determined assay order states of the discrete areas.

41 Claims, 9 Drawing Sheets

(52) U.S. Cl.
CPC .............. *G01N 2035/00831* (2013.01); *G01N 2035/00841* (2013.01); *G01N 2035/00861* (2013.01); *G16H 10/40* (2018.01)

(56) References Cited

U.S. PATENT DOCUMENTS

| | | | |
|---|---|---|---|
| 2010/0294840 A1 | 11/2010 | Barry | |
| 2012/0200396 A1* | 8/2012 | Cobb | G01N 35/00732 340/10.6 |
| 2013/0065797 A1* | 3/2013 | Silbert | G01N 1/31 73/304 C |

FOREIGN PATENT DOCUMENTS

| | | | | |
|---|---|---|---|---|
| WO | WO-2011024012 A1 * | 3/2011 | ......... | B65D 21/0219 |
| WO | 2012/093261 A1 | 7/2012 | | |

OTHER PUBLICATIONS

EPO Communication pursuant to Article 94(3) EPC, European Application No. 18720068.8, Jan. 31, 2022.
PCT Search Report and Written Opinion, International application No. PCT/US2018/025463, Jul. 19, 2018.
EPO Communication pursuant to Article 94(3) EPC, European Application No. 18720068.8, Dec. 13, 2023.

* cited by examiner

METHOD OF PROCESSING A SAMPLE

BACKGROUND

Field

Embodiments of this disclosure relate to labels, receptacles, systems, and methods for automatic sample processing.

Background

Healthcare service providers, such as doctors, physician assistants, nurse practitioners, and nurses, very often do not possess the equipment needed to perform a desired test (also referred to as an "assay") on a collected sample. As a consequence, healthcare providers frequently send collected samples to a laboratory to perform one or more desired assays. To ensure timely and appropriate treatments, healthcare providers generally desire rapid, reliable, and low cost laboratory services for performing the ordered assays on a sample. Thus, the "total turnaround time" from collecting a sample at a collection site (for example, a healthcare provider's office) to receiving the final test results from the laboratory is an important factor to healthcare providers.

Total turnaround time includes two primary components: (1) a "collection-and-delivery component" that covers the time required to collect a sample and deliver it to a laboratory for processing, and (2) a "laboratory component" that covers the time from which the laboratory receives the collected sample to the time the assay on the collected sample is completed and a result is rendered. Accordingly, total turnaround time for laboratory services can be reduced by reducing the collection-and-delivery component and/or the laboratory component.

SUMMARY

In some embodiments, a method of processing a sample in a receptacle having one or more assay order states on the receptacle includes receiving the receptacle containing the sample. The receptacle includes a plurality of discrete areas. Each area has a known association with a different assay. The receptacle also includes a plurality of assay-identifying indicia. Each assay-identifying indicia indicates the assay associated with a respective area of the plurality of discrete areas. The receptacle also includes patient-identifying indicia. The method also includes automatically determining assay order states of the plurality of discrete areas, and performing at least one assay on the sample, using one or more automatic sample processing instruments, based on the determined assay order states of the plurality of discrete areas.

In some embodiments, performing the at least one assay on the sample based on the determined assay order states of the plurality of discrete areas includes performing the assay associated with each area of the plurality of discrete areas having an altered assay order state. In some embodiments, performing the at least one assay on the sample based on the determined assay order states of the plurality of discrete areas includes performing the assay associated with each area of the plurality of discrete areas having an unaltered assay order state.

In some embodiments, automatically determining the assay order states of the plurality of discrete areas includes using a reader of the one or more automatic sample processing instruments. In some embodiments, automatically determining the assay order states of the plurality of discrete areas comprises using a hand-held reader operatively coupled to the one or more automatic sample processing instruments.

In some embodiments, automatically determining the assay order states of the plurality of discrete areas comprises automatically determining whether machine-readable indicia are present within the plurality of discrete areas. The machine-readable indicia can be a barcode or an instrument mark.

In some embodiments, automatically determining the assay order states of the plurality of discrete areas comprises automatically determining whether there are any physical deformations present within the plurality of discrete areas.

In some embodiments, the method of processing a sample in the receptacle also includes receiving a form comprising patient-identifying indicia having a known association with the patient-identifying indicia of the receptacle. The patient-identifying indicia of the form can include a first barcode, and the patient-identifying indicia of the receptacle can include a second barcode. The first barcode and the second barcode can be identical in some embodiments.

In some embodiments, the method also includes entering (or accessioning) information on the form into a laboratory information system. Entering the information on the form into the laboratory information system can be automatic. Entering the information on the form into the laboratory information system can occur concurrently with or after performing the at least one assay on the sample based on the determined assay order states of the plurality of discrete areas. The method can also include associating the results of the at least one assay performed on the sample with the information entered into the laboratory information system based on the patient-identifying indicia of the receptacle.

In some embodiments, each assay associated with a respective area of the plurality of discrete areas determines the presence or absence of a different analyte or analytes in the sample.

The patient-identifying indicia of the receptacle can be machine readable in some embodiments, and automatically determining the assay order states of the plurality of discrete areas can include using the machine-readable, patient-identifying indicia as a reference point for locating the plurality of discrete areas of the receptacle.

In some embodiments, the patient-identifying indicia of the receptacle comprise a unique serial number.

In some embodiments, a method for ordering one or more assays to be performed on a sample includes collecting the sample within a receptacle. The receptacle includes a plurality of discrete areas, each area having a known association with a different assay. The receptacle also includes a plurality of assay-identifying indicia, each indicia indicating the respective assay associated with a respective area of the plurality of discrete areas. And the receptacle can include first patient-identifying indicia on the receptacle.

The method can also include altering an assay order state of at least a first area of the plurality of discrete areas in some embodiments. In some embodiments, the first area is associated with an assay to be performed on the sample. In some embodiments, the first area is associated with an assay not to be performed on the sample.

In some embodiments, the method also includes altering the assay order state of at least a second area of the plurality of discrete areas.

In some embodiments, altering the assay order state of the first area includes marking, using a writing instrument, at least a portion of the first area. The portion of the first area can include at least a portion of machine-readable indicia. In some embodiments, altering the assay order state of the first area can include removing a label disposed on the receptacle covering, at least in part, the first area of the plurality of discrete areas. In some embodiments, removing the label includes exposing machine-readable indicia. In other embodiments, the label may include machine-readable indicia. In some embodiments, the altering the assay order state of the first area can include applying a pressure exceeding a threshold to the first area, thereby deforming the first area.

In some embodiments, the plurality of discrete areas, the plurality of assay-identifying indicia, and the patient-identifying indicia are disposed on a label disposed on the receptacle.

In some embodiments, the method also includes removing a label disposed on the receptacle that includes second patient-identifying indicia having a known association with the first patient-identifying indicia. And the method can include affixing the label on a form comprising patient-related information.

In some embodiments, the method includes packaging together the receptacle having the first patient-identifying indicia and the form having the affixed label that includes the second patient-identifying indicia into a container. The first patient-identifying indicia can include a first barcode, and the second patient-identifying indicia can include a second barcode. The first barcode and the second barcode can be identical.

In some embodiments, the first patient-identifying indicia on the receptacle are provided before collecting the sample within the receptacle. In some embodiments, the first patient-identifying indicia on the receptacle are provided after collecting the sample within the receptacle.

In some embodiments, a sample receptacle for ordering assays to be performed by one or more automatic sample processing instruments includes a body defining a chamber for containing a sample, and a first label coupled to the body. The first label can include a plurality of discrete areas each configured to be altered from a first assay order state to a second assay order state by a user. Each area of the plurality of discrete areas has a known association with a different assay. The first label can also include a plurality of assay-identifying indicia, each indicia indicates the respective assay associated with a respective area of the plurality of discrete areas.

In some embodiments, the label also includes first patient-identifying indicia. The first patient-identifying indicia can be machine readable. The first patient-identifying indicia can include a barcode. In some embodiments, the sample receptacle also includes a second label removably disposed on the first label. The second label can include second patient-identifying indicia having a known association with the first patient-identifying indicia. The second label can be configured to be reapplied to another surface after being removed from the receptacle. The second patient-identifying indicia can be machine readable. The second patient-identifying indicia can include a barcode. The first patient-identifying indicia and the second patient-identifying indicia can be identical.

In some embodiments, the label also includes manually-inputted, human-readable, patient-identifying indicia.

In some embodiments, the first patient-identifying indicia can include an RFID signal.

In some embodiments, at least one of the first assay order state and the second assay order state can include machine-readable indicia readable by an automatic reader.

In some embodiments, each of the discrete areas can include a removable label having the respective machine-readable indicia. The presence of the removable label can define the first assay order state of the respective discrete area, and the absence of the removable label can define the second assay order state of the respective discrete area.

In some embodiments, each of the discrete areas includes a removable label covering the respective machine-readable indicia. The presence of the removable label can define the first assay order state of the respective discrete area, and the absence of the removable label can define the second assay order state of the respective discrete area.

In some embodiments, each of the discrete areas is configured to be marked by a writing instrument. In some embodiments, the first assay order state can include a blank area. In some embodiments, each of the discrete areas is configured to be deformed in response to an applied pressure exceeding a threshold.

In some embodiments, each of the discrete areas is visibly demarcated. Each of the discrete areas can be visibly demarcated by a geometric shape. In some embodiments, each of the discrete areas is visibly demarcated by a unique geometric shape.

In some embodiments, the label also includes information about the assays associated with the plurality of discrete areas.

Further features and advantages of the embodiments, as well as the structure and operational of various embodiments, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

DESCRIPTION OF THE DRAWINGS

The accompanying drawings, which are incorporated herein and form a part of the specification, illustrate the embodiments and, together with the description, further serve to explain the principles of the embodiments and to enable a person skilled in the relevant art(s) to make and use the embodiments.

The features and advantages of the embodiments will become more apparent from the detailed description set forth below when taken in conjunction with the drawings, in which like reference characters identify corresponding elements throughout.

DETAILED DESCRIPTION

Figure 1:
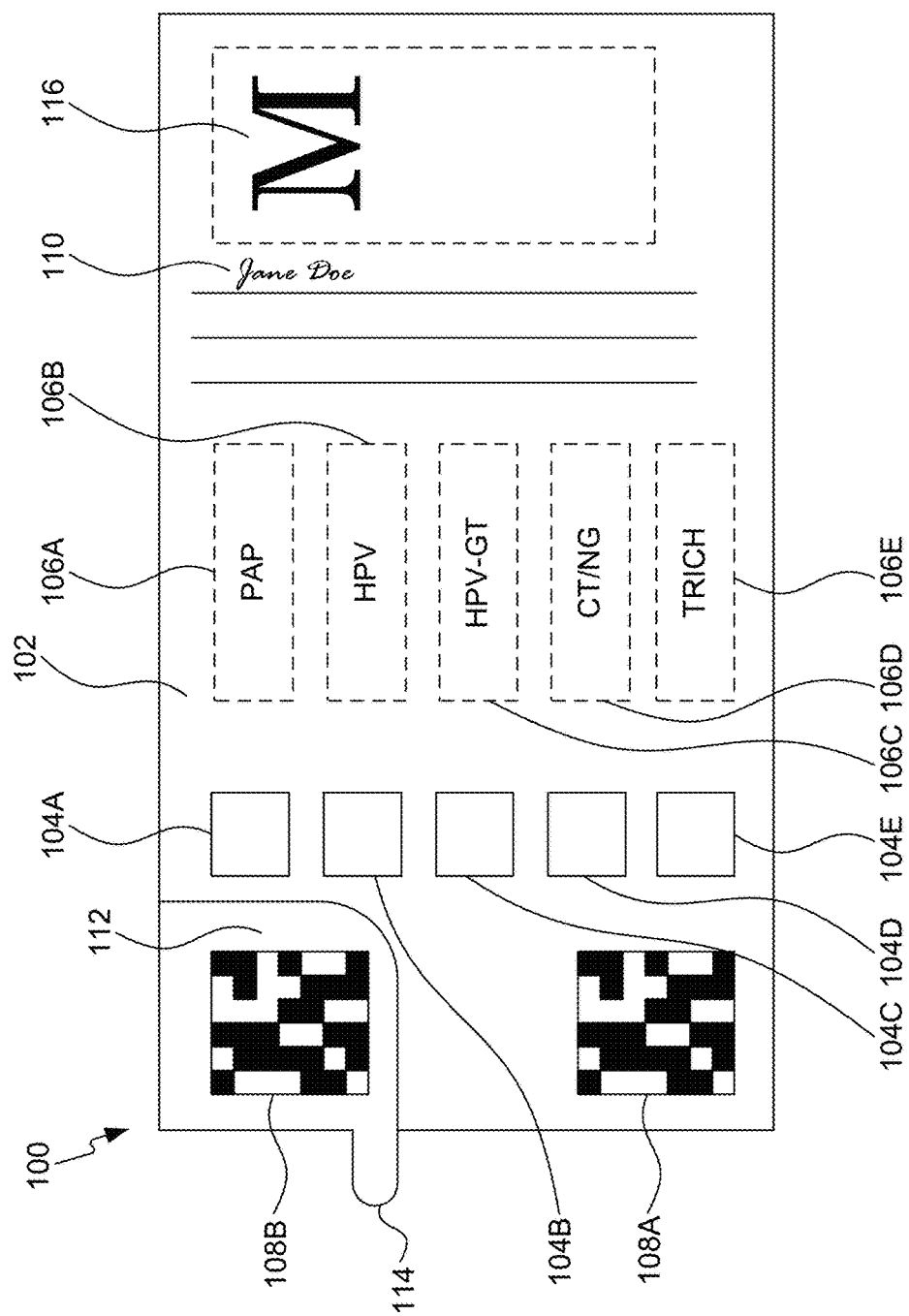
FIG. 1 is a plan view of a label having unaltered assay order states, according to an embodiment.

The present disclosure will now be described in detail with reference to embodiments thereof as illustrated in the accompanying drawings. References to "one embodiment," "an embodiment," "some embodiments," "an exemplary embodiment," "for example," "an example," "exemplary," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein, "a" or "an" means "at least one" or "one or more."

As used herein, a "sample" refers to any material to be analyzed, regardless of the source. The material may be in its native form or any stage of processing (e.g., the material may be chemically altered or it may be one or more components of a sample that have been separated and/or purified from one or more other components of the sample). A sample may be obtained from any source, including, but not limited to, animal, environmental, food, industrial, or water sources. Animal samples include, but are not limited to, peripheral blood, plasma, serum, bone marrow, urine, bile, mucus, phlegm, saliva, cerebrospinal fluid, stool, biopsy tissue including lymph nodes, respiratory tissue or exudates, gastrointestinal tissue, cervical swab samples, semen or other body or cellular fluids, tissues, or secretions. Samples can be diluted or contained within a receptacle containing diluents, transport media, preservative solution, or other fluids. As such, the term "sample" is intended to encompass samples contained within a diluent, transport media, and/or preservative or other fluid intended to hold a sample.

As used herein, a "sample receptacle" refers to any type of fluid container, including, for example, a tube, vial, cuvette, cartridge, microtiter plate, etc., that is configured to contain a sample in its native form or at any stage of processing.

As used herein, a "sample processing instrument" refers to any instrument capable of performing a processing step on a sample contained within a receptacle. A sample processing instrument includes any instrument capable of performing an assay on a sample and rendering a result. For example, a sample processing instrument includes any instrument capable of performing an assay on a sample to determine the presence of an analyte in the sample. Any instrument capable of performing, for example, a hybridization assay, a molecular assay including a nucleic acid-based amplification reaction, a sequencing assay, an immunoassay, or chemistry assay on a sample is included in this definition of a sample processing instrument. Exemplary sample processing instruments capable of performing an assay on a sample to determine the presence of an analyte in the sample include the Tigris® and Panther® systems sold by Hologic, Inc., Bedford, MA, the diagnostic instrument systems disclosed in U.S. Pat. No. 6,335,166, as well as any of the diagnostic instruments disclosed in U.S. Patent Application Publication No. 2016/0060680, published Mar. 3, 2016. A sample processing instrument also includes any instrument that only performs sample preparation steps and is not capable of analyzing a sample and/or rendering a result. For example, an instrument that transfers a sample from one receptacle to another receptacle and/or adds one substance to a receptacle containing a sample, but does not perform the final steps needed to render a result. An instrument that only performs sample preparation steps to isolate and/or purify an analyte of interest is a sample processing instrument. An exemplary sample processing instrument that only performs sample preparation steps is the Tomcat® system sold by Hologic, Inc., Bedford, MA and the instrument systems disclosed in U.S. Pat. No. 9,335,336.

In the context of this application, "automatic" and "automatically" refers to a non-manual operation performed by, for example, mechanical and/or electrical apparatuses, processes, and/or systems that take the place of solely manual or human operations. That is, "automatic" and "automatically" are not references to an entirely manual operation.

In the context of this application, "assay order state" is a condition that indicates whether or not a particular assay should be performed on a sample.

In the context of this application, the term "indicia" includes one or more indicators despite the plural verb conjugation used throughout the application. For example, "indicia" covers only one indicator (e.g., one barcode), as well as two or more indicators (e.g., two or more barcodes).

Exemplary Labels and Sample Receptacles

Some embodiments include receptacles, each having one or more automatically determinable assay order states on the receptacles. And some embodiments include systems and methods for processing samples contained within such receptacles based on the one or more automatically determinable assay order states. Samples contained within such receptacles can be automatically processed (for example, one or more steps of one or more ordered assays can be performed on the samples) based on the one or more automatically determinable assay order states on the receptacles containing the samples. In some embodiments, the disclosed receptacles, systems, and methods can reduce the total turnaround time to perform desired assays by reducing at least one of the collection-and-delivery component or the laboratory component of total turnaround.

In some embodiments, the one or more automatically determinable assay order states can be defined by one or more portions of a receptacle body or a label disposed on a receptacle body. FIG. 1 illustrates a label 100 according to one such embodiment. Label 100 is configured to be disposed on a body of receptacle, for example, on an exterior surface of a receptacle body. In some embodiments, label 100 includes a substrate 102. Substrate 102 can be flexible such that label 100 conforms to a non-planar surface of the receptacle body. Substrate 102 can be made of paper, plastic, or any other suitable material. In some embodiments, an adhesive layer is disposed on a surface of substrate 102, adhering label 100 to the receptacle body.

The shape and size of label 100, when viewed in plan, can vary depending on the shape and size of the receptacle body on which label 100 is disposed. For example, although label 100 has a substantially rectangular shape when viewed in plan as shown in FIG. 1, label 100 can have any other suitable shape.

In some embodiments, label 100 includes one or more discrete areas that define, at least in part, the one or more automatically determinable assay order states. For example, as shown in FIG. 1, label 100 includes five discrete areas 104A-104E. Each of discrete areas 104A-104E can have a known association with a particular type of assay. For example, in some embodiments, each discrete area 104A-104E has a known association with an assay for determining the presence or absence of different analytes in the sample. Exemplary assays can include assays for determining the presence or absence of infectious microorganisms (e.g., microorganisms that cause sexually transmitted diseases such as chlamydia, gonorrhea, certain high-risk strains of human papillomavirus (HPV), and the *Trichomonas vaginalis* parasite). Exemplary assays can also include cytology assays such as cervical cancer screening assays (e.g., a Pap test), and assays used to assist physicians in assessing the risk of pre-term birth. Exemplary assays can also include blood screening assays, which can be used to detect various infectious agents, such as HIV type-1 (HIV-1), HIV type-2 (HIV-2), hepatitis A virus (HAV), hepatitis B virus (HBV), hepatitis C virus (HCV), hepatitis E virus (HEV), West Nile virus, Zika virus, and Parvovirus.

In some embodiments, the plurality of discrete areas 104A-104E can have known associations with assays commonly ordered for a particular patient demographic, such as a specific gender, ethnicity, patients subject to a certain health condition, patients at certain geographic locations, patients of a certain age, etc. For example, as shown in FIG. 1, the plurality of discrete areas 104A-104E have known associations with assays associated with women's health. For example, in some embodiments, discrete area 104A can have a known association with an assay for determining the presence or absence of abnormal cervical cells in a sample that are indicative of cancer or conditions that may develop into cancer (e.g., a Pap test). Discrete area 104B can have a known association with an assay for determining the presence or absence of human papillomavirus (HPV) in a sample (e.g., an HPV test). Discrete area 104C can have a known association with another assay for determining the presence or absence of specific types of human papillomavirus such as types 16, 18, and 45 (e.g., an HPV genotype test). Discrete area 104D can have a known association with an assay for determining the presence or absence of *Chlamydia trachomatis* (CT) and *Neisseria gonorrhoeae* (NG) in a sample (e.g., a CT/NG assay). And discrete area 104E can have a known association with an assay for determining the presence or absence of the protozoan parasite *Trichomonas vaginalis* in a sample. In some embodiments, one or more of the discrete areas 104A-104E and the associated one or more assays can be omitted. And in some embodiments, one or more additional discrete areas having known associations with one or more additional assays for other analytes, for example, Mycoplasma genitalium, can also be included. In some embodiments not shown, discrete areas 104A-104E can have known associations with different types of assays associated with women's health.

Again, in some embodiments, the associated assays are assays commonly ordered for demographics different than women, for example, men, or both men and women of a certain age.

In some embodiments, the associated assays include at least (a) one assay for determining the presence or absence of a particular analyte, and (b) one assay for determining the genotype of that particular analyte (if present) in the sample. The pairing of these two assays is sometimes referred to as "co-testing" or "reflex testing."

In some embodiments, the associated assays are assays typically performed by blood banks. For example, assays to determine the presence or absence of various blood-borne infectious agents, such as human immunodeficiency virus type-1 (HIV-1), human immunodeficiency virus type-2 (HIV-2), hepatitis A virus (HAV), hepatitis B virus (HBV), hepatitis C virus (HCV), hepatitis E virus (HEV), West Nile virus (WNV), Zika virus, and parvovirus.

In some embodiments, the associated assays are for patients that have known infections. For example, assays can monitor the viral load or quantified amount of virus in a patient's system.

In some embodiments, the associated assays are for patients at risk for healthcare-associated infections. For example, the assays can determine the presence or absence of central line-associated blood-borne infections, catheter-associated urinary tract infections, ventilator-associated pneumonia, and surgical site infections. Such healthcare-associated infections can include, for example, methicillin-resistant *Staphylococcus aureus* (MRSA).

Label 100 can also include assay-identifying indicia that visually indicate to a healthcare provider (who is ordering the assays) the assay associated with a respective discrete area 104A-104E. For example, as shown in FIG. 1, label 100 includes a plurality of assay-identifying indicia 106A-106E for each of discrete areas 104A-104E. Assay-identifying indicia 106A-106E can be positioned proximate to respective discrete areas 104A-104E as shown in FIG. 1. In some embodiments, assay-identifying indicia 106A-106E include alphanumeric characters or graphical symbols. For example, as shown in FIG. 1, assay-identifying indicia 106A include alphanumeric characters "PAP," indicating that discrete area 104A is associated with an assay (e.g., a Pap assay) for determining the presence or absence of abnormal cervical cells in a sample that are indicative of cancer or a condition that may develop into cancer. Assay-identifying indicia 106B include alphanumeric characters "HPV" indicating that discrete area 104B is associated with an assay for determining the presence or absence of human papillomavirus in a sample. Assay-identifying indicia 106C include alphanumeric characters "HPV-GT" indicating that discrete area 104C is associated with an assay for determining the presence or absence of specific genotypes of human papillomavirus (for example types 16, 18, and 45) in a sample. Assay-identifying indicia 106D include alphanumeric characters "CT/NG" indicating that discrete area 104D is associated with an assay for determining the presence or absence of *Chlamydia trachomatis* (CT) and *Neisseria gonorrhoeae* (NG) in a sample. Assay-identifying indicia 106E include alphanumeric characters "TRICH" indicating that discrete area 104E is associated with an assay for determining the presence or absence of *Trichomonas vaginalis* in a sample. Although the assay-identifying indicia 106A-106E include alphanumeric characters "PAP," "HPV," "HPV-GT," "CT/NG," and "TRICH" in the embodiment of FIG. 1, any other suitable alphanumeric characters can be used to provide the respective indication of the assay associated with the respective discrete area.

In some embodiments not shown, assay-identifying indicia 106A-106E can include only letters or only numbers having a known association with a particular assay. In some embodiments not shown, assay-identifying indicia 106A-106E can include graphical symbols, for example, icons, images, or geometric shapes, having a known association with a particular assay. These associations can be provided to a healthcare provider when the healthcare provider receives a batch of sample receptacles having labels 100.

Discrete areas 104A-104E and assay-identifying indicia 106A-106E collectively function as a menu on the receptacle, itself, of possible assays to perform on a sample. This menu can remind a healthcare provider about the possible assays that can be performed on the sample. For example, if a sample is collected from a female patient, the discrete areas 104A-104E and assay-identifying indicia 106A-106E can collectively form a menu of possible women's health related assays to perform on the sample. This menu can also simplify the collection process at the healthcare provider site since the possible assays to order are already on the sample receptacle, which can reduce the collection-and-delivery component of total turnaround time.

In some embodiments, label 100 includes more than or less than five discrete areas having known associations with particular assays. As shown in FIG. 1, discrete areas 104A-104E are vertically aligned on label. In some embodiments, discrete areas 104A-104E can be horizontally aligned or arranged in any other suitable configuration.

In some embodiments, each discrete area 104A-104E is visibly demarcated from each other, for example, by a geometric shape such as a square, rectangle, or any other suitable shape. As shown in FIG. 1, each discrete area 104A-104E is visibly demarcated from each other by a square (as shown in FIG. 1). In some embodiments not shown, each discrete area is visibly demarcated by a unique geometric shape to further distinguish each discrete area. For example, discrete area 104A could be demarcated by a square, while discrete area 104B is demarcated by a circle, and so on.

Figure 6:
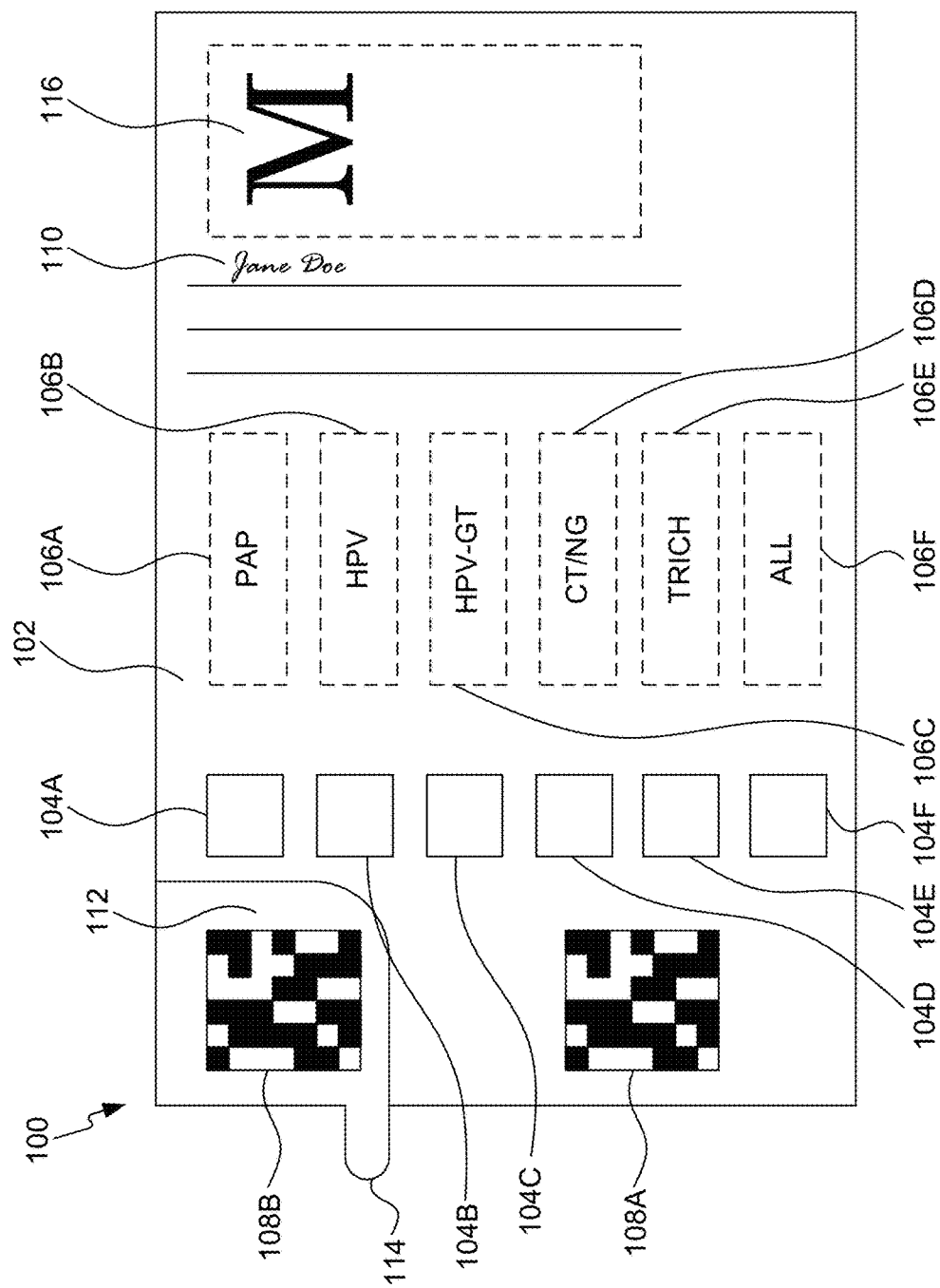
FIG. 6 is a plan view of a label having unaltered assay order states, according to an embodiment.

In some embodiments, label 100 includes a discrete area (for example, discrete area 104F in FIG. 6), that has a known association with each assay associated with the other discrete areas on label 100 (for example, discrete areas 104A-104E in FIG. 6). As shown in FIG. 6, label 100 can also include assay-identifying indicia 106F (for example, the alphanumeric text "ALL") that visually indicate to a healthcare provider that discrete area 104F is associated with each assay associated with the other discrete areas 104A-104E.

In some embodiments, label 100 can also include one or more patient-identifying indicia that can be used to identify the source of a sample. In some embodiments, the patient-identifying indicia are machine readable—capable of being read or sensed by a device. Machine-readable indicia include, but are not limited to, barcodes (e.g., 1D or 2D barcodes), printed or handwritten alphanumeric text, symbols, marks, or colors that can be read or sensed by a device. In some embodiments, the machine-readable indicia are read or sensed by the device using vision recognition software or optical character recognition software. For example, as shown in FIG. 1, label 100 can include at least one barcode 108A encoded with information that associates a sample within a respective sample receptacle to a specific patient. Barcode 108A can be a one- or two-dimensional barcode. Exemplary two-dimensional barcodes express information in two directions, for example, in the horizontal and vertical directions, and include stacked barcodes and matrix barcodes. Exemplary two-dimensional barcodes include, for example, Aztec codes, PDF417 codes, MaxiCodes, Codablock codes, Data Matrix codes, and QR codes. In some embodiments, barcode 108A can be printed on label 100 at the collection site or prior to being received at the collection site during the manufacturing process of label 100.

In some embodiments, barcode 108A encodes at least a patient identifier such as a patient name, an assigned patient identification number, or a unique serial number that has a known association with the patient from whom the sample was collected.

In some embodiments, barcode 108A may also encodes patient metadata (for example, date of birth, age, sex, gender, height, or weight), medical history, any other desired patient information, as well as the healthcare provider requesting the assay, the date the sample was collected, the collection site, and other suitable information.

In some embodiments, label 100 also includes second patient-identifying indicia that have a known association with first patient-identifying indicia. For example, in some embodiments, label 100 includes a second barcode 108B encoded with a patient identifier such as a patient name, an assigned patient identification number, or a unique serial number that has a known association with the patient from which the sample was collected. Barcode 108B can be encoded with the same information encoded by barcode 108A. In some embodiments, barcode 108A and barcode 108B are identical. Barcode 108B can be a one- or two-dimensional barcode.

Label 100 includes a second label 112 configured to be removably disposed on at least one of the receptacle body and a portion of substrate 102 of label 100, in some embodiments. And barcode 108B can be disposed on removable second label 112. Label 112 can be configured to be reapplied to another surface after being removed from substrate 102 of label 100. The other surface can be, for example, a paper order form completed by the healthcare provider ordering the test. Label 112 can include an adhesive layer that releasably couples label 112 to substrate 102 of label 100, and to the other surface to which label 112 is subsequently reapplied. In some embodiments, second label 112 includes a tab 114 extending away from the main body of second label 112 such that a user can easily grasp tab 114 and peel label 112 away from substrate 102 of label 100. Label 112 can be made of the same material as substrate 102 in some embodiments. In some embodiments, label 112 is made from a different material than substrate 102 of label 100.

In some embodiments (not shown), the second label 112 overlaps the entire label 100 and is identical to label 100. In such embodiments, instead of marking label 100, the healthcare provider marks second label 112, and the marking is transferred to underlying label 100. For example, the underside of second label 112, the topside of label 100, or both, includes a pressure-sensitive copy material such that, when a healthcare provider applies pressure (e.g., marks with a pen) to second label 112, the pressure causes the pressure-sensitive copy material to transfer the mark to the underlying label 100. Label 112 can then be removed and reaffixed to another object, for example, a test order form. In some embodiments, after the collection site writes patient-identifying indicia 110 on label 112 and marks one or more desired discrete areas 104A-104E, the healthcare provider can remove label 112 from label 100, and place label 100 on the order form. Underlying label 100 may contain all the same information as label 112.

In some embodiments, the one or more patient-identifying indicia include an RFID signal generated by an RFID tag on label 100. The RFID signal can be encoded with a patient identifier such as a patient name, an assigned patient identification number, or a unique serial number that has a known association with other patient-identifying indicia or the patient from whom the sample was collected.

In some embodiments, the patient-identifying indicia also include indicia readable by a human. Human-readable, patient-identifying indicia can, for example, be composed of alphanumeric characters that spell the patient name, express an assigned patient identification number, or express a unique serial number. As shown in FIG. 1, label 100 includes human-readable, patient-identifying indicia 110 that spell the patient name, "Jane Doe." Human-readable, patient-identifying indicia 110 can be manually inserted by a healthcare provider or printed on label 100 at the collection site, or during the manufacturing process of label 100. In some embodiments, an area can be visibly designated for receiving human-readable, patient-identifying indicia 110. For example, as shown in FIG. 1, this area can be designated by series of lines.

In some embodiments, label 100 also includes a portion 116 that may include information about the menu of options defined by discrete areas 104A-104E and assay-identifying indicia 106A-106E. For example, portion 116 can include a brand name associated with the assay manufacturer, as well as any other suitable information regarding the assay menu and instructions regarding sample care.

In some embodiments, each of the plurality of discrete areas 104A-104E can be configured to be altered from a first assay order state to a second assay order state by a user. Depending on the embodiments, either the first assay order state or the second assay order state indicates whether the assay having the known association with the respective discrete area should be performed on a sample.

In some embodiments, at least one of the first assay order state and the second assay order state of each discrete area 104A-104E can include machine-readable indicia that can be read or sensed by a device. Exemplary assay-order-state defining machine-readable indicia include, but are not limited to, barcodes (e.g., 1D or 2D barcodes), printed or handwritten alphanumeric text, symbols, marks, or colors that can be read or sensed by a device. In some embodiments, the machine-readable indicia are read or sensed by the device using vision recognition software or optical character recognition software. The machine-readable indicia of the first or second assay order state can be read by an automatic reader, such as a laser barcode scanner or an image capture device (e.g., a camera).

In some embodiments, discrete areas 104A-104E are configured to be altered from the first assay order state to the second assay order state by marking at least a portion of the respective discrete area 104A-104E with a writing instrument such as a pen, pencil, marker, or printer. In some embodiments, the material composing substrate 102 of label 100 is configured to be marked and to retain the marks for an extended period of time (e.g., about the typical total turnaround time). For example, the material composing substrate 102 can be configured such that the marks do not wear off during ordinary shipping and processing of the receptacle on which label 100 is disposed.

Figure 2:
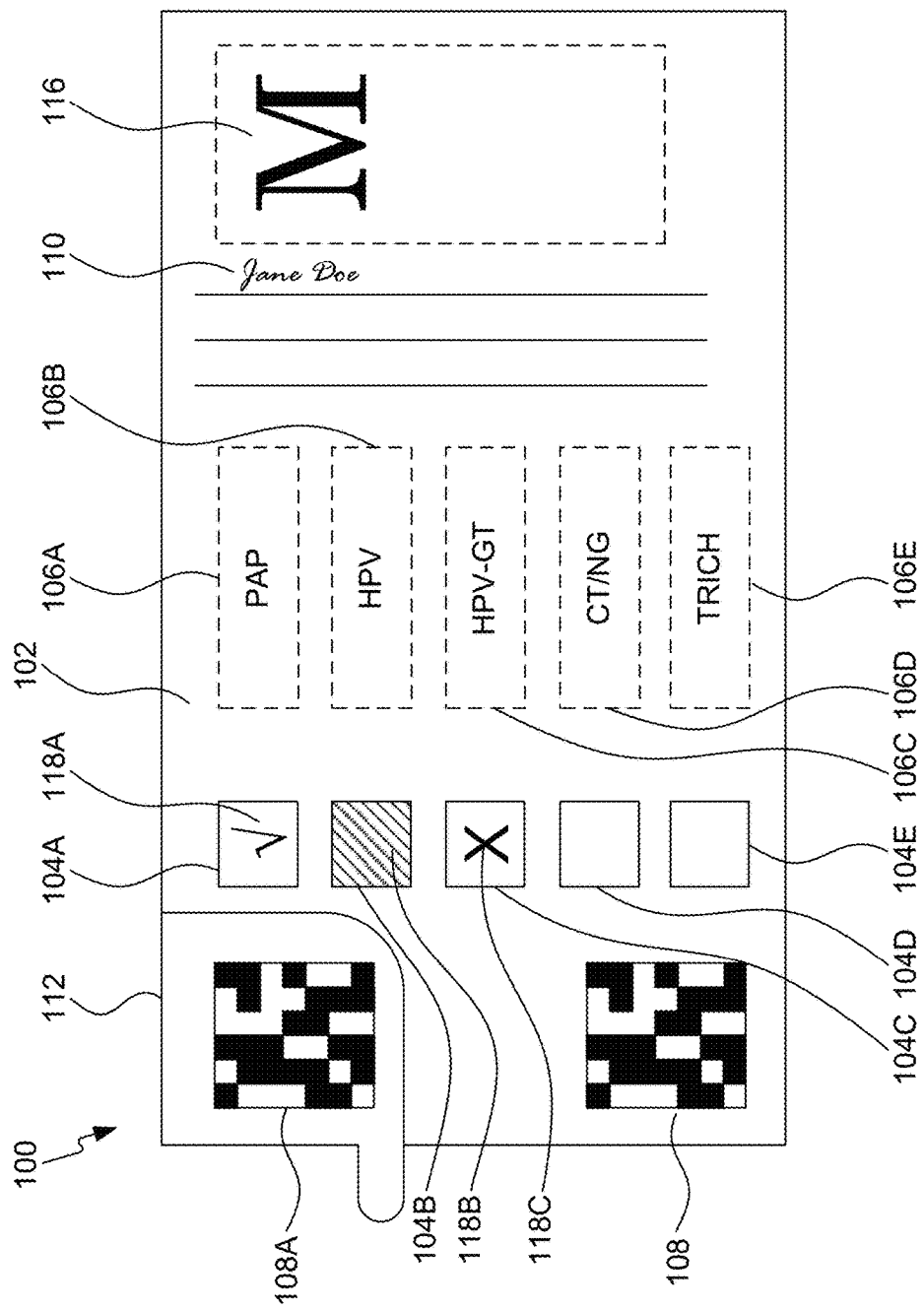
FIG. 2 is a plan view of the label of FIG. 1 having altered assay order states, according to an embodiment.

For example, FIG. 1 illustrates discrete areas 104A-104E having first, unaltered assay order states according to an embodiment. As shown in FIG. 1, the first, unaltered assay order state of each discrete area 104A-104E is defined by a blank area. In some embodiments, each of areas 104A-104E is configured to be marked by a writing instrument. FIG. 2 illustrates discrete areas 104A-104C in second, altered assay order states, and discrete areas 104D and 104E in first, unaltered assay order states according to an embodiment. As shown in FIG. 2, a healthcare provider marked discrete areas 104A-104C, respectively, with a check mark 118A, a complete fill-in mark 11B, and an "X" 118C. A user can user any other suitable machine-readable marks to alter the assay order state of the desired discrete areas 104A-104E.

In some embodiments, instead of marking discrete areas 104A-104E with a writing instrument, the user can apply stickers, labels, or any other suitable attachable object to discrete areas 104A-104E to alter the respective assay order states. In some embodiments, the sticker or label at least partially obstructs machine-readable indicia in the respective covered discrete area of areas 104A-104E.

Figure 3:
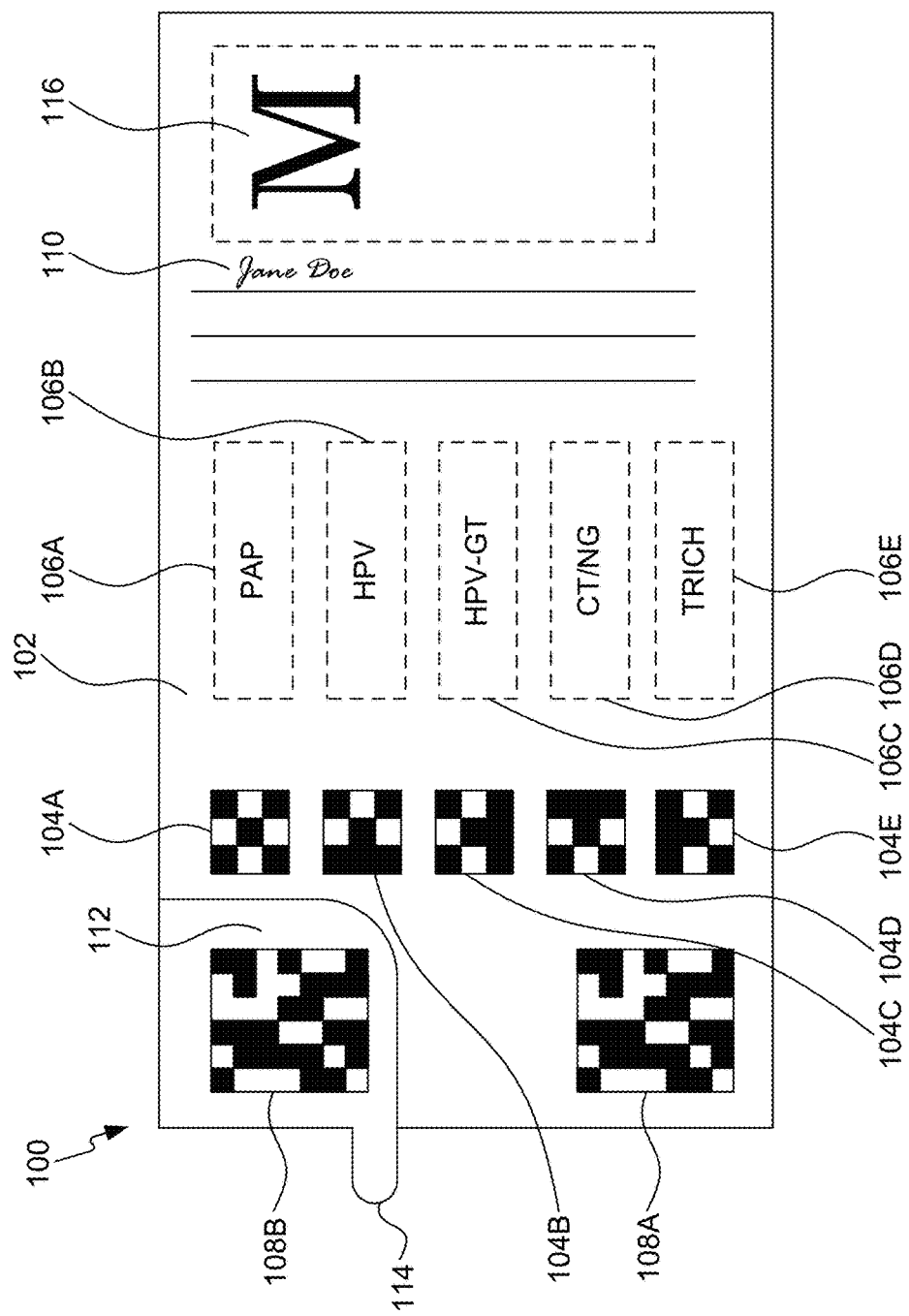
FIG. 3 is a plan view of a label having unaltered assay order states, according to another embodiment.
Figure 4:
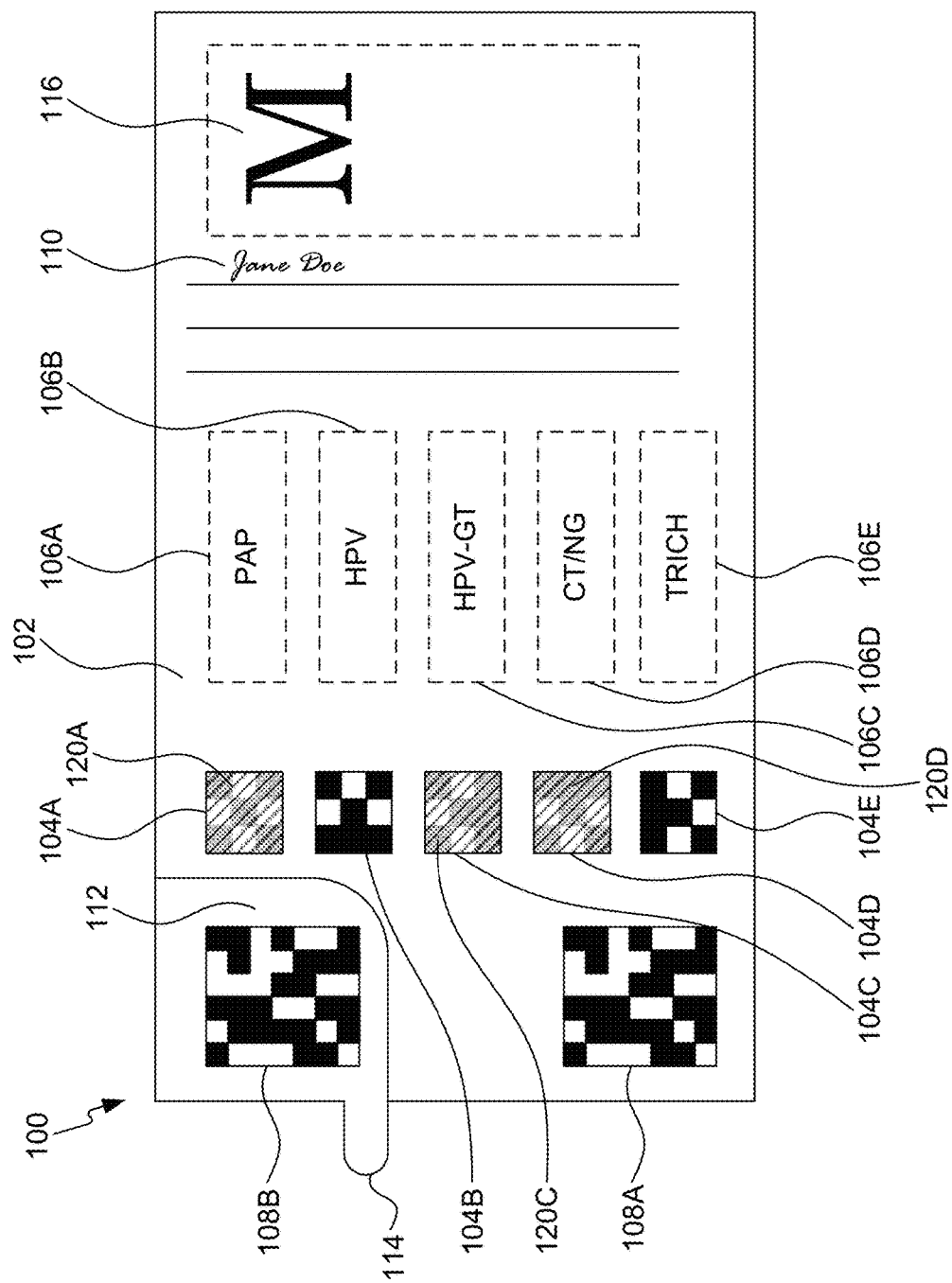
FIG. 4 is a plan view of the label of FIG. 3 having altered assay order states, according to an embodiment.

FIG. 3 illustrates discrete areas 104A-104E having first, unaltered assay order states according to another embodiment. As shown in FIG. 3, the first, unaltered assay order state of each discrete areas 104A-104E is defined by machine-readable indicia, for example, a two-dimensional barcode as shown in FIG. 3, within each respective discrete areas 104A-104E. In some embodiments, each machine-readable indicator is unique as shown in FIG. 3. In other embodiments (not shown), the machine-readable indicia are the same. Each of discrete area 104A-104E can be configured to be marked by a writing instrument. FIG. 4 illustrates discrete areas 104A, 104C, and 104D in second, altered assay order states, and discrete areas 104B and 104E in first, unaltered assay order states according to an embodiment. As shown in FIG. 4, a healthcare provider marked, as desired, discrete areas 104A, 104C, and 104D by filling in solid box marks 120A, 120C, and 120D. Any suitable means (for example, a writing instrument, an attachable label or sticker, or a stamp) for fully or partially marking discrete areas 104A-104E can be used.

As shown in FIG. 4, box marks 120A, 120C, and 120D substantially cover the entire respective area discrete areas 104A, 104C, and 104D. In other embodiments, the marks may only partially obstruct the underlying machine-readable indicia in a manner that is detectable by an automatic reader.

Figure 5:
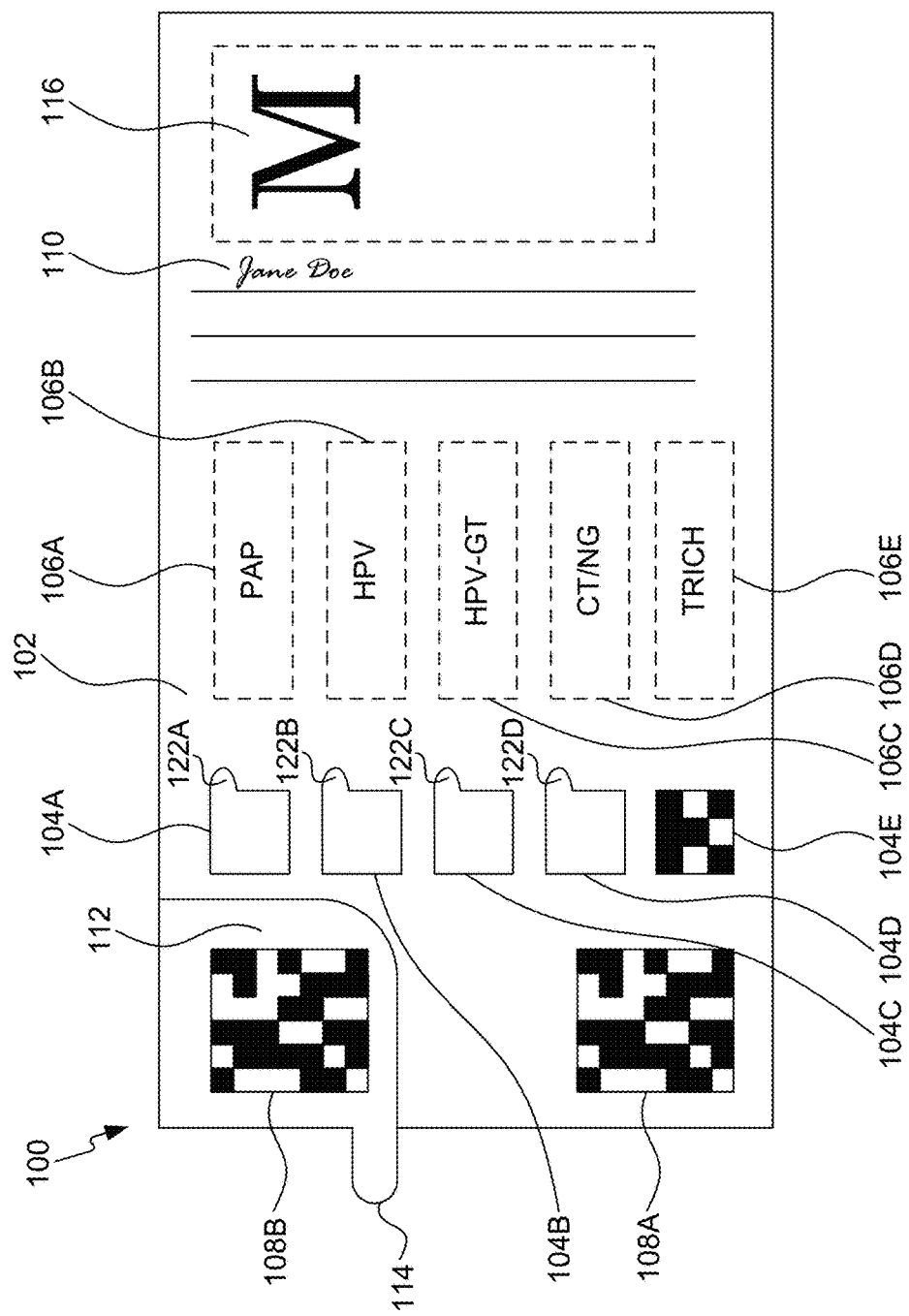
FIG. 5 is a plan view of a label having unaltered and altered assay order states, according to another embodiment.

In some embodiments, first, unaltered assay order states are defined by a removable label covering respective machine-readable indicia in discrete areas 104A-104E. And each discrete area 104A-104E can be altered to the second assay order state by removing the respective removable label. FIG. 5 illustrates an exemplary embodiment. Labels 122A-122D cover discrete areas 104A-104D, respectively, to define the first, unaltered assay order state of each discrete areas. As shown in FIG. 5, a corresponding label has been removed to uncover machine-readable indicia in discrete area 104E, thereby defining the second, altered assay order state of discrete area 104E.

In some embodiments, labels 122 can each have a machine-readable indicator (e.g., a barcode), and discrete areas 104A-104E can be blank. Labels 122 having machine-readable indicia covering discrete areas 104A-104E can define the first, unaltered assay order states of discrete areas 104A-104E. Labels 122 can be removed to uncover the underlying blank discrete areas, thereby defining the second, altered assay order state of the discrete areas.

Figure 9:
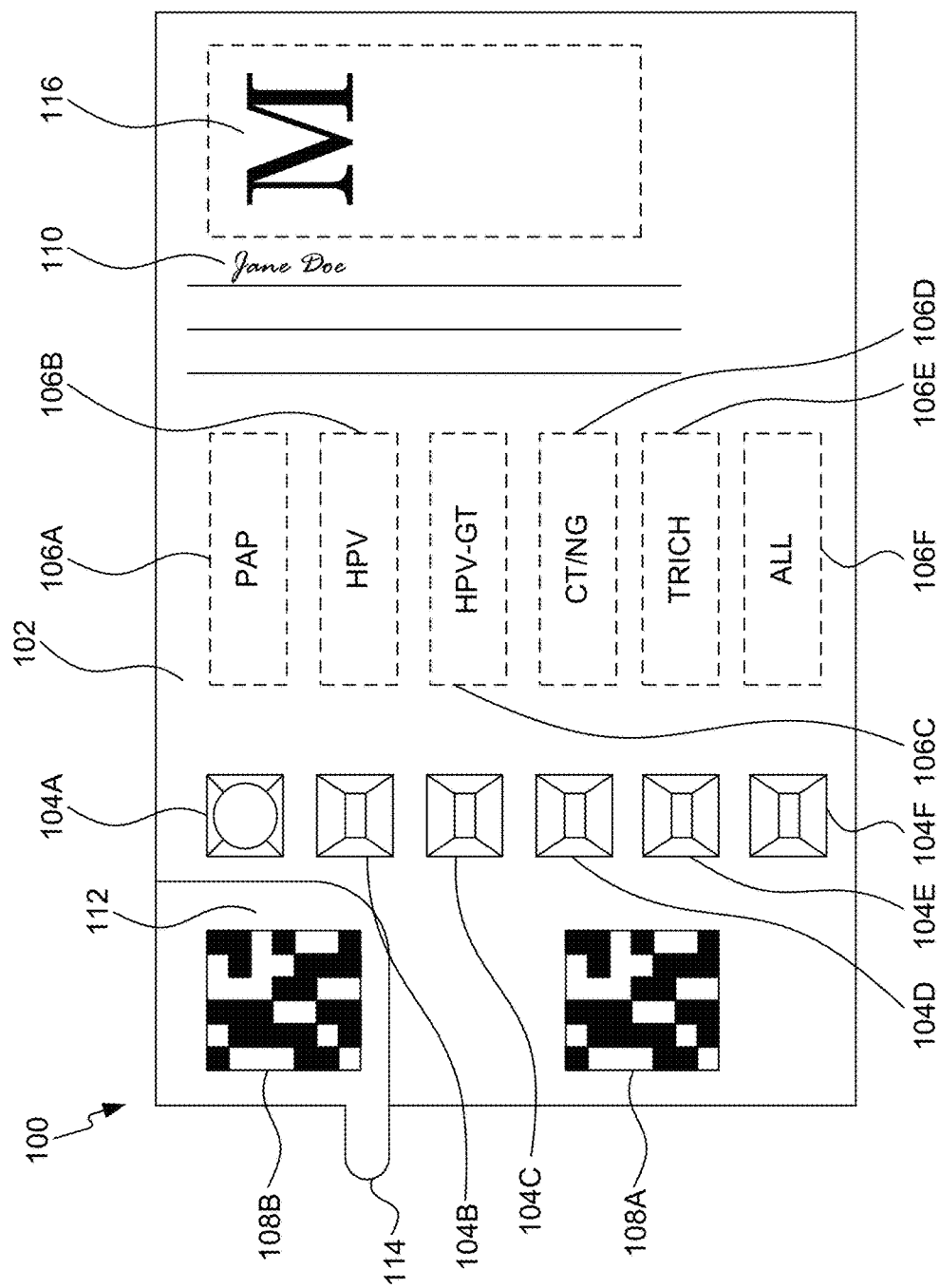
FIG. 9 is a plan view of a label having unaltered and altered assay order states, according to an embodiment.

In some embodiments, first and second assay order states are defined by the physical shape of discrete areas 104A-104E. For example, discrete areas 104A-104E can be configured to deform in response to an applied pressure exceeding a threshold. And the first, unaltered assay order states of discrete areas 104A-104E can be defined by non-deformed shapes of discrete areas 104A-104E, and the second, altered state of discrete areas 104A-104B can be defined by the deformed discrete areas 104A-104E. FIG. 9 illustrates an exemplary physical deformation embodiment. Discrete areas 104B-104F protrude outward from substrate 102, thereby defining the first, unaltered assay order states. Discrete area 104A is depressed to be substantially flat, thereby defining the second, altered assay order state.

Figure 7:
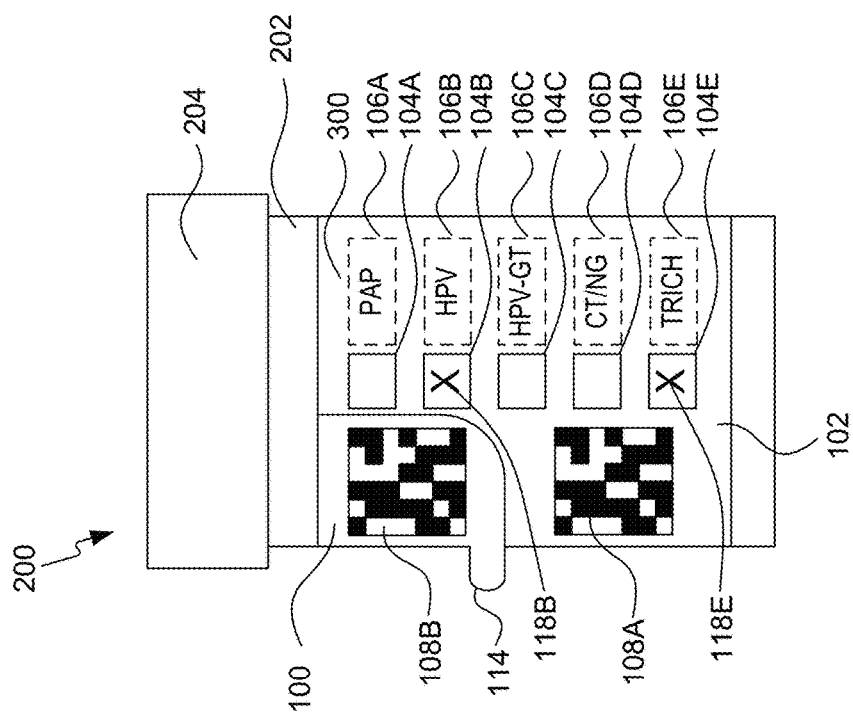
FIG. 7 is a side view of a sample receptacle having a label, according to an embodiment.

FIG. 7 illustrates an exemplary receptacle 200 having label 100 disposed thereon, according to an embodiment. Label 100 can have an adhesive backing that adheres label 100 to an exterior surface of a body 202 of receptacle 200. Body 202 defines a chamber for containing a sample. Receptacle 200 can also include a cap 204 configured to fluidly seal the chamber containing the sample. Body 202 can have any variety of configurations (e.g., shapes and sizes) that are suitable for containing a sample in its native form or at any stage of processing. In some embodiments, body 202 can be a cylindrical tube.

Exemplary Assay Sample Processing Methods Using Exemplary Labels and Receptacles Any one of the above described labels and receptacles can be used to process a sample, and various sample processing embodiments are described below referencing generally FIG. 8, which schematically illustrates system components used in these sample processing embodiments.

Collection and Assay Ordering

Starting at the collection site, for example, a healthcare provider's office, a healthcare provider (e.g., a physician, physician's assistant, nurse practitioner, nurse, phlebotomist, or technician) collects a sample from a patient, and provides the sample to the chamber defined by receptacle body 202 of receptacle 200. The healthcare provider can then fluidly seal the sample within the chamber using cap 204.

In some embodiments, label 100 is already disposed on receptacle body 202 when the sample is provided to the chamber defined by body 202 of receptacle 200. In some embodiments, label 100 is disposed on receptacle body 202 (e.g., affixed to receptacle body 202 with an adhesive backed label) after the sample is collected.

Next, in some embodiments, the healthcare provider alters an assay order state of a least one discrete area 104A-104E based on the desired assay(s) to be performed on the sample. In some embodiments, the healthcare provider alters the assay order states of any discrete area having a known association with a desired assay to be performed on the sample. For example, referencing FIG. 8, if the healthcare provider wants to order (1) an assay for determining the presence or absence of human papillomavirus (HPV) in a sample and (2) an assay for determining the presence or absence of *Chlamydia trachomatis* (CT) and *Neisseria gonorrhoeae* (NG) in the sample, the healthcare provider alters the assay order states of discrete areas 104B and 104D, which have known associations with these assays as indicated by respective assay-identifying indicia 106B and 106D. For example, the healthcare provider can alter the assay order states by marking discrete areas 104B and 104D with marks 118B and 118D using a writing instrument such as a pencil, pen, marker, or printer. In other embodiments, the healthcare provider can alter the assay order states of discrete areas 104B and 104D by removing labels disposed on the receptacle covering machine-readable indicia in each of discrete areas 104B and 104D, thereby exposing the machine-readable indicia. In other embodiments, the healthcare provider can alter the assay order states of discrete areas 104B and 104D by applying stickers or labels to cover machine-readable indicia in each of discrete areas 104B and 104D. In other embodiments, the healthcare provider alters the assay order states of discrete areas 104B and 104D by applying a pressure exceeding a threshold to each of discrete areas 104B and 104D, thereby deforming the first area.

In some of such embodiments, if a healthcare provider desires that all assays indicated on label 100 be performed, the healthcare provider alters the assay-order state of each discrete area 104A-104E. And in some of such embodiments in which label 100 includes a discrete area (for example, discrete area 104F in FIG. 6) that has a known association with each assay associated with the other discrete areas (for example, discrete areas 104A-104E) on label 100, the healthcare provide alters the assay-order state of only that particular discrete 104F.

In some embodiments, the healthcare provider alters the assay order states of any discrete areas having a known association with an assay that is not desired to be performed on the sample. For example, referencing FIG. 8, if the healthcare provider desires that (1) an assay for determining the presence or absence of abnormal cervical cells in a sample that are indicative of cancer or conditions that may develop into cancer (a "PAP" assay), (2) an HPV genotype test for determining the presence or absence of specific types of human papillomavirus, such as types 16, 18, and 45 of HPV (an "HPV-GT" assay), and (3) an assay for determining the presence or absence of the protozoan parasite *Trichomonas vaginalis* be performed on the sample (a "TRICH" assay), the healthcare provider will alter the assay order states of discrete areas 104B and 104D, which are associated with non-desired assays, by, for example, applying marks 118B and 118D to the respective areas 104B and 104D. In such embodiments, if a healthcare provider desires that all assays indicated on label 100 be performed, the healthcare provider does not alter any assay-order state of discrete areas 104A-104E.

At the collection site, the healthcare provider can also ensure that one or more patient-identifying indicia (for example, barcode 108A or manually-inputted, human-readable indicia 110) are provided on receptacle 200 (for example, on label 100) containing the sample. In some embodiments, the patient-identifying indicia, such as barcode 108A, are disposed on receptacle 200 before receptacles 200 are received at the collection site. For example, the collection site purchases receptacles 200 having label 100, including barcode 108A, already affixed to receptacle body 202. In some embodiments, the patient-identifying indicia, such as barcode 108A and manually-inputted, human-readable indicia 110, are provided at the collection site. For example, label 100 can be printed with barcode 108A at the collection site and disposed on receptacle 200, and the healthcare provider can manually add indicia 110, using a writing instrument, at the collection site while collecting the sample.

Figure 8:
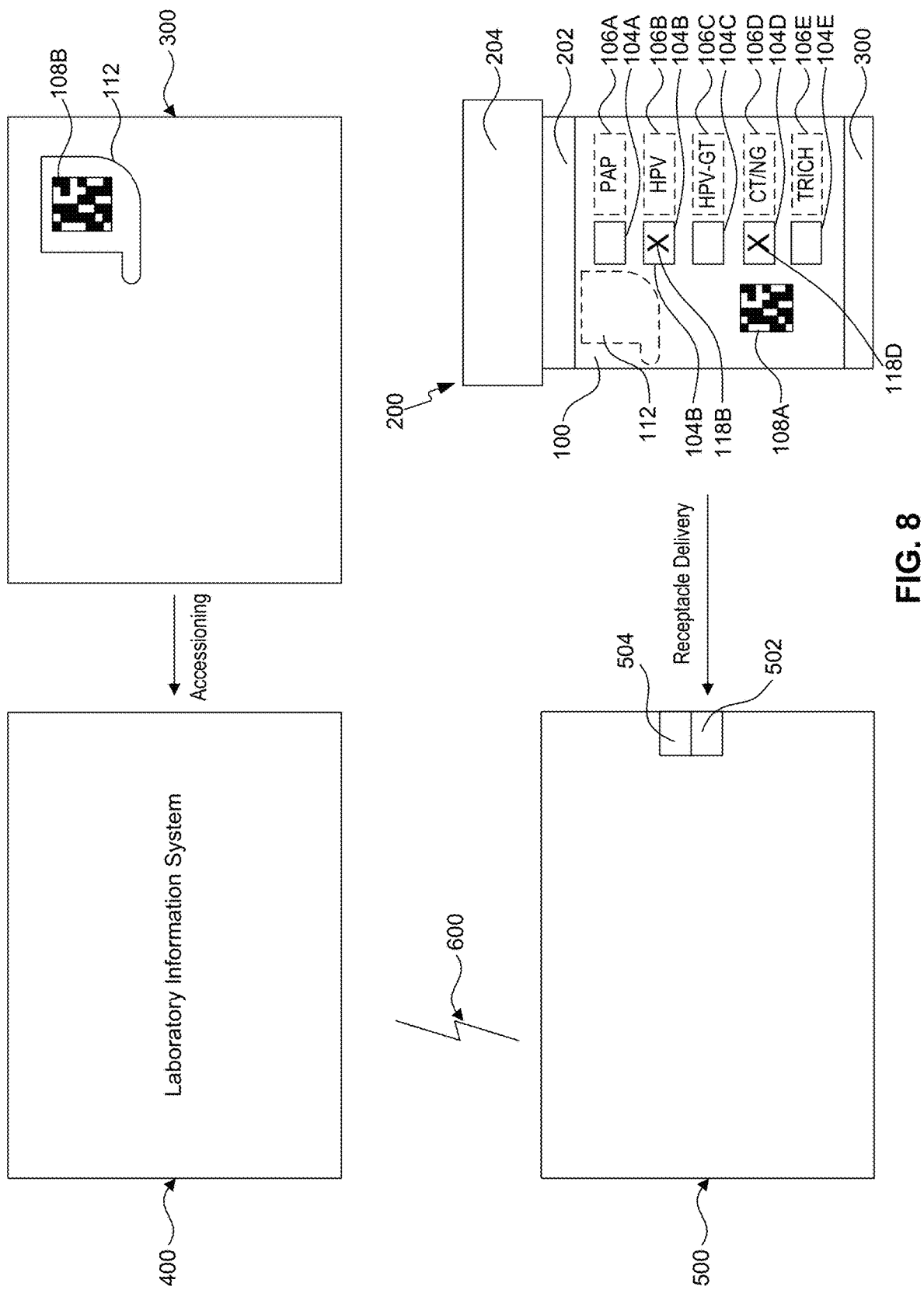
FIG. 8 is a schematic diagram of an automatic system for processing a sample, according to an embodiment.

In some embodiments, before, concurrently, or after, the sample is collected within receptacle body 202 at the collection site, the healthcare provider at the collection site removes second label 112, which also includes machine-readable, patient-identifying indicia (for example, barcode 108B), and affixes second label 112 to an order form 300 (schematically illustrated in FIG. 8). In some embodiments, order form 300 confirms the desired assays that should be performed on the sample (as indicated by the altered assay order states) and includes human-readable, patient-identifying indicia (in addition to machine-readable barcode 108B on second label 112), as well as identifying information about the ordering healthcare provider. In some embodiments, the order from 300 also includes patient or healthcare provider metadata. For example, such metadata can include the following patient metadata: name, date of birth, age, sex, symptoms, medical history, height, weight, and contact information. And for example, such metadata can further include the following healthcare provider metadata: collection date, collection site, name of person collecting sample, physician, and collection site contact information.

In other embodiments, order form 300 may omit any indication of what assays should be performed on the sample. That is, in some embodiments, the only indication of what assays are to be performed on the sample is found on label 100 on sample receptacle 200.

Then in some embodiments, order form 300 having second label 112 affixed thereto and receptacle 200 containing the sample are packaged together in a container (e.g., a bag, envelop, or box) and delivered to a laboratory to perform the ordered assays. In some embodiments, the laboratory receiving the packaged order form 300 and sample containing receptacle 200 has one or more sample processing instruments that are configured to automatically perform one or more steps of the ordered assays, as indicated by the assay order states of the plurality of discrete areas 104A-104E.

In some embodiments, just the sample containing receptacle 200 is sent to the laboratory—the physical order form 300 can be omitted from the process. In such embodiments, sample containing receptacle 200 may include all the necessary information to process the sample. For example, the sample containing receptacle 200 includes patient-identifying indicia (e.g., barcode 108A and manually-inputted, patient-identifying indicia 110), and the indication of which assays to be performed, which are represented by the assay order states of discrete areas 104A-104E.

In some embodiments in which the physical order form 300 is omitted, an electronic version of the order form can be communicated to the laboratory over a communication network. The electronic order form can include any of the information described above regarding physical order form 300. In such embodiments, the electronic order form can be associated with sample containing receptacle 200 when receptacle 200 is received at the laboratory.

Accessioning

Next, after sample containing receptacle 200 is received at the laboratory along with physical order form 300, the laboratory accessions (i.e., enters information) the assay order into the laboratory's computerized laboratory information system (LIS) 400. In some embodiments, the assay order is accessioned into the LIS 400 based on information on order form 300, information on receptacle 200, or both. LIS 400 can be, in some embodiments, a computerized system of one or more devices that uses, stores, and updates assay and patient data in a database. For example, LIS 400 can store patient records, ordered assays, and the results of ordered assays. LIS 400 can be connected to and communicate, over a communication network 600, with one or more automatic sample processing instruments 500 configured to perform one or more steps of one or more assays. For example, network 600 can be a local area network (LAN), in some embodiments.

In some embodiments, the assay order is manually accessioned into LIS 400. In some manual embodiments, a laboratory technician manually inputs information, for example, by using a keyboard or touch screen, from order form 300 into LIS 400. This information can include patient-related information (e.g., patient name, patient identification number, metadata, or any other patient-related information), and the assays to be performed on the sample contained in the receptacle 200 associated with order form 300.

In some embodiments, the assay-order accessioning process is a combination of manual input operations (e.g., a laboratory technician using a keyboard or touch screen) and automatic input operations (e.g., using a reader such as a laser barcode reader or image capture device (e.g., camera)). In some mixed-mode accessioning embodiments, at least some patient-related information is inputted into the LIS 400 during an automatic operation. For example, a reader can be used to decode patient-related information encoded on barcode 108B, and this decoded information can be automatically stored in an electronic record of the LIS 400. In some embodiments, this decoded information includes a unique serial number, and any other patient-identifying information. In some embodiments, the laboratory technician can then manually enter the non-automatically-entered information on order form 300 (for example, ordered assay information, patient metadata, and healthcare provider metadata) into LIS 400. During accessioning, the laboratory technician can also manually enter into the LIS any other patient information on order form 300.

In some embodiments, the assay-order accessioning process is substantially entirely automatic. For example, order form 300 can be placed in a machine queue to be automatically read by a reader utilizing, for example, optical text recognition software or machine-readable indicia decoding software.

Assay Sample Processing

Processing of the sample contained within receptacle 200 can start before, concurrently, or after the assay order is accessioned into LIS 400.

During sample processing, the sample containing receptacle 200 is either manually or automatically delivered to one or more sample processing instruments 500 for performing one or more steps of the ordered one or more assays. In some embodiments, a laboratory technician initiates this sample processing by either placing the sample containing receptacle 200 into an automatic queue (for example, a portion of an automatic conveyor system) operatively coupled to one or more sample processing instruments 500 that are configured to automatically perform the one or more ordered assays, or by placing the sample containing receptacle 200 into an input rack configured to be received, at an input bay, by the one or more sample processing instruments 500. In automatic conveyor system embodiments, the conveyor system can route the sample receptacle 200 to the appropriate one or more sample processing instruments 500 for performing the desired assay. Exemplary conveyor systems include any one of the embodiments disclosed in U.S. Non-provisional application Ser. No. 15/434,968, filed Feb. 16, 2017, which is incorporated herein by reference.

In some embodiments, the sample containing receptacle 200 is placed in the automatic queue or received in an input rack at an input bay of sample processing instruments 500 before the assay order is accessioned into LIS 400. The assays to be performed on the sample are indicated directly on receptacle 200 by the assay order states of the plurality of discrete areas 104A-104E having known associations with particular assays. Accordingly, sample processing instrument 500 can start processing the sample based on this indication, and does not need to wait until the assay order is accessioned into LIS 400. Sample receptacle 200 also includes patient-identifying indicia (e.g., encoded in barcode 108A) such as the patient name, patient identification number, or an unique serial number. Accordingly, the results of the one or more assays performed on the same can subsequently be matched to the patient record in LIS 400 using the patient-identifying indicia (for example, barcode 108A) on sample receptacle 200. For example, the results of the one or more assays can be stored in a buffer memory until a matching patient record is entered into LIS 400. At that point, the assay results can be associated with the appropriate patient record in LIS 400. Since sample processing can start before the assay order is actually accessioned into LIS 400, the laboratory component of total turnaround time from the time of receipt to results can be reduced in some embodiments.

In other embodiments, the sample containing receptacle 200 is placed in the automatic queue or received in an input rack at an input bay of sample processing instruments 500 after the sample is accessioned into LIS 400.

During processing of a sample, the steps of a single assay can be performed on one, two, or more than two sample processing instruments 500. For example, in some embodiments, a sample receptacle 200 can be first delivered to an instrument (for example, a Tomcat® system sold by Hologic, Inc.) that only performs sample preparation steps and is not capable of analyzing a sample and/or rendering a result, itself. Such sample preparation instruments can transfer (e.g., aliquot) a portion of the sample in receptacle 200 to another receptacle and/or add one or more substances to a receptacle containing the sample, but does not actually perform the assay steps that render a result about an analyte of interest.

Then the receptacle that contains the prepared sample can be transferred, for example, via an automatic conveyor system or manually, to one or more other sample processing instruments 500 configured to perform the remaining steps of the ordered assay(s). For example, the remaining steps can be steps for actually determining the presence or absence of the analyte of interest in the sample. Exemplary sample processing instruments capable of performing such steps include the Tigris® and Panther® systems sold by Hologic, Inc. In some embodiments, such sample processing instruments 500 transfer a portion of the sample (e.g., an aliquot) in the received receptacle to another receptacle and/or add one or more substances to a receptacle containing the sample.

In some embodiments, the assays can be performed on a single sample processing instrument—for example, all sample preparation and analytical steps of a single assay are performed by a single sample processing instrument.

In some embodiments, one or more readers 502 are coupled to at least one of (a) one or more sample processing instruments 500 or (b) an automatic conveyor system operatively coupled to the one or more sample processing instruments 500. Reader 502 can be configured to the automatically determine the assay order states of the plurality of discrete areas (for example, areas 104A-104D in FIG. 1) on sample receptacle 200.

Reader 502 can be an component of an automatic conveyor system in some embodiments. For example, once the receptacle 200 is placed in the queue of the automatic conveyor system, a reader 502 can automatically determine the assay order states of the plurality of discrete areas 104A-104D on sample receptacle 200. Based on the determined assay order states, the automatic conveyor system can route receptacle 200 to the appropriate one or more sample processing instruments 500 for performing the steps of the ordered assay(s).

Reader 502 can be an integral component of sample processing instrument 500 in some embodiments. For example, the receptacle is introduced to sample processing instrument 500 via, for example, an automatic conveyor or manually inserted rack, and an internally located reader 502 of sample processing instrument 500 can automatically determine the assay order states of the plurality of discrete areas 104A-104D on sample receptacle 200. Or reader 502 can be a hand-held reader that a user manually operates, and hand-held reader 502 is either wired or wirelessly connected to instrument 500. For example, a user can manually scan sample receptacle 200 using hand-held reader 502 and then introduce the sample receptacle to sample processing instrument 500 via, for example, an automatic conveyor or manually inserted rack.

In some embodiments, reader 502 can be, for example, an image capture device (e.g., a camera) or laser barcode reader configured to detect or identify which discrete areas of the plurality of discrete areas 104A-104E have an altered or unaltered assay order state. In some embodiments, the altered or unaltered assay order states of the plurality of discrete areas 104A-104E are automatically determined using reader 502 and, for example, image recognition software or optical character recognition software. For example, reader 502 can detect whether machine-readable indicia are present within any of the plurality of discrete areas 104A-104E. Machine-readable indicia can be a barcode (see, for example, FIGS. 3 and 4) or a writing instrument mark (see, for example, FIGS. 1, 2, 5, and 6).

In some embodiments, reader 502 can be, for example, an image capture device (e.g., a camera) configured to detect the presence or absence of a physical deformation of a respective area of the plurality of discrete areas 104A-104E. In some embodiments, the altered or unaltered assay order states of the plurality of discrete areas 104A-104E are automatically determined using reader 502 and, for example, image recognition software configured to detect a deformation from a captured image.

In some embodiments in which the machine-readable, patient-identifying indicia include barcode 108A, reader 502 can use barcode 108A as a point of reference (also called a "fiducial marker") to locate each of the discrete areas 104A-104E. For example, if the position of each discrete area 104A-104E relative to barcode 108A is known, reader 502 can locate discrete areas 104A-104E by first locating barcode 108A. In some embodiments, reader 502 uses indicia other than barcode 108A on label 100 or receptacle 200 as a point of reference (i.e., as a fiducial marker) to locate each of the discrete areas 104A-104E. For example, reader 502 may use a geometric features such as a boundary of label 100 (e.g., a corner) as a reference. Or for example, reader 502 may use text, shapes, or other barcodes on label 100 or receptacle 200 as the point of reference.

Sample processing instrument 500 can then perform one or more steps of the one or more assays on a sample contained within sample receptacle 200 based on the determined assay order states of the plurality of discrete areas 104A-104E. The steps of the one or more assays can be performed in batch or random access modes. In some embodiments, sample processing instrument 500 aliquots portion(s) of the sample in receptacle 200 into one or more other receptacles for performing one or more steps of the assay. For example, sample processing instrument 500 can have instructions stored in memory for automatically performing one or more steps of the one or more assays knowingly associated with each of discrete areas 104A-104E. Each assay-specific set of instructions can indicate to which stations within sample processing instrument 500 a receptacle containing the sample is transported, which reagents are added to a receptacle containing the sample and at what concentrations, which environmental conditions (e.g., temperature and agitation) are applied to a receptacle containing the sample, and what characteristics (e.g., light intensity at a specific wavelength) are examined to determine the presence or absence of an analyte in the sample. These instructions can vary for each assay associated with the plurality of discrete areas 104A-104E. Referencing FIG. 8, sample processing instrument 500 can perform assays associated with discrete areas 104A, 104C, and 104E that are not marked, or discrete areas 104B or 104D that are marked, depending on the embodiment, based on the stored instructions in sample processing instrument 500.

In some embodiments, sample processing instrument 500 performs one or more steps of the one or more assays based on the determined assay order states of the plurality of discrete areas 104A-104E, and based on scheduling instructions stored in memory of the sample processing instrument 500. The scheduling instructions can indicate the order in which the one or more steps of the one or more assays are performed. For example, according to exemplary scheduling instructions, if an assay for determining the presence or absence of a particular analyte and an assay for determining the genotype of that particular analyte (if present) in the sample are both ordered, sample processing instrument 500 may first perform the assay for determining the presence or absence of a particular analyte, and then (if the first assay determines that the particular analyte is present) perform the assay for determining the genotype of that particular analyte, according to the scheduling instructions.

In some embodiments, the scheduling instructions of sample processing instrument 500 can provide the order in which certain types of assays are performed. For example, certain assay may be processed before other types of assays according to the scheduling instructions. The priority can be determined based on patient risk, in some embodiments. The priority can also be determined based on instructions from the requesting healthcare provider, in some embodiments.

In some embodiments, sample processing instrument 500 includes another reader 504 configured to decode patient-identifying indicia (for example, machine-readable barcode 108A, or an RFID signal generated by an RFID tag on sample receptacle 200) on sample receptacle 200. Reader 504 can be, for example, a laser barcode reader, an image capture device (e.g., a camera), or an RFID reader. In other embodiments, reader 502 can both detect which discrete areas of the plurality of discrete areas 104A-104D have an altered or unaltered assay order state, and decode machine-readable, patient-identifying indicia on label 100. In such embodiments, reader 504 may be omitted.

Reader 504 can decode patient-identifying information (such as a patient name, a patient identification number, or a unique serial number having a known association with the patient) on sample receptacle 200 and subsequently use the patient-identifying information to track the sample within sample processing instrument 500. The decoded patient-identifying information can also be used to associate the results of the one or more performed assays with the appropriate patient record in LIS 400.

After the one or more assays are performed using one or more sample processing instruments 500, the results of the one or more assays can be communicated to LIS 400 via communication network 600. LIS 400 can then associate the results with the patient record in LIS 400, which was created during accessioning. If the assay order has not yet been accessioned, the results of the one or more assays can be stored in a buffer memory until the respective patient record is created in LIS 400. If the assay order has already been accessioned, the results of the one or more assay can be immediately associated with the patient record stored in LIS 400. At that point, the results can be validated and released to the requesting healthcare provider.

Hardware and Software

Aspects of this disclosure are implemented via control and computing hardware components, user-created software, data input components, and data output components. Hardware components include computing and control modules (e.g., system controller(s)), such as microprocessors and computers, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to an operator for providing information to the operator, for example information as to the status of the instrument or a process being performed thereby, or such outputs may comprise inputs to other processes and/or control algorithms. Data input components comprise elements by which data is input for use by the control and computing hardware components. Such data inputs may comprise position sensors, motor encoders, as well as manual input elements, such as graphic user interfaces, keyboards, touch screens, microphones, switches, manually-operated scanners, voice-activated input, etc. Data output components may comprise hard drives or other storage media, graphic user interfaces, monitors, printers, indicator lights, or audible signal elements (e.g., buzzer, horn, bell, etc.).

Software comprises instructions stored on non-transitory computer-readable media which, when executed by the control and computing hardware, cause the control and computing hardware to perform one or more automatic or semi-automatic processes.

While the present disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations are not intended to convey that the disclosure requires features or combinations of features other than those expressly recited in the claims. Accordingly, the present disclosure is deemed to include all modifications and variations encompassed within the spirit and scope of the following appended claims.

All documents referred to herein are hereby incorporated by reference herein. No document, however, is admitted to be prior art to the claimed subject matter.

Furthermore, those of the appended claims which do not include language in the "means for performing a specified function" format permitted under 35 U.S.C. § 112(f) are not intended to be interpreted under 35 U.S.C. § 112(f) as being limited to the structure, material, or acts described in the present specification and their equivalents.

What is claimed is:

1. A method of processing a sample in a receptacle having one or more assay order states, the method comprising the steps of:
   collecting the sample within the receptacle, wherein the receptacle comprises a label, and wherein the label comprises:
   a plurality of discrete areas having known associations with multiple assays, each of the plurality of discrete areas having a known association with one assay of the multiple assays, and each of the plurality of discrete areas being configured to be altered from a first assay order state to a second assay order state, wherein for each of the plurality of discrete areas:
   the first assay order state is defined by a removable label covering machine-readable indicia in the discrete area, the first assay order state indicating that the one assay having the known association with the discrete area is not to be performed, the second assay order state is defined by exposure of the machine-readable indicia in the discrete area, the second assay order state indicating that the one assay having the known association with the discrete area is to be performed, a plurality of assay-identifying indicia, each assay-identifying indicia indicating the one assay having the known association with the corresponding discrete area of the plurality of discrete areas, and each assay-identifying indicia including alphanumeric characters or graphical symbols, and patient-identifying indicia; and altering at least one discrete area of the plurality of discrete areas from the first assay order state to the second assay order state by removing the corresponding removable label, thereby exposing the machine-readable indicia associated with the at least one discrete area.

2. The method of claim 1, wherein the machine-readable indicia comprise a barcode.

3. The method of claim 1, wherein the multiple assays determine the presence or absence of different analytes in the sample.

4. The method of claim 1, wherein the patient-identifying indicia of the receptacle are machine-readable.

5. The method of claim 1, wherein the patient-identifying indicia of the receptacle comprise a unique serial number.

6. The method of claim 1, wherein the plurality of discrete areas and the plurality of assay-identifying indicia are arranged in a series of rows and columns on the label.

7. The method of claim 6, wherein each discrete area and the corresponding assay-identifying indicia are located in the same row.

8. The method of claim 1, further comprising the steps of:

automatically determining assay order states of the plurality of discrete areas by determining which of the plurality of discrete areas has been altered from the first assay order state to the second assay order state; and performing the one assay associated with each of the plurality of discrete areas determined to have the second assay order state.

9. The method of claim 8, wherein the automatically determining step comprises using a reader of an automatic sample processing instrument.

10. The method of claim 8, wherein the automatically determining step comprises using a hand-held reader operatively coupled to an automatic sample processing instrument.

11. The method of claim 8, further comprising the step of receiving a form comprising patient-identifying indicia having a known association with the patient-identifying indicia of the receptacle.

12. The method of claim 11, wherein the patient-identifying indicia of the form comprise a first barcode, and wherein the patient-identifying indicia of the receptacle comprise a second barcode.

13. The method of claim 12, wherein the first barcode and the second barcode are identical.

14. The method of claim 11, further comprising the step of entering information on the form into a laboratory information system.

15. The method of claim 14, wherein the entering step is automatic.

16. The method of claim 14, wherein the entering step occurs concurrently with or after the performing step.

17. The method of claim 14, further comprising the step of associating results of each of the multiple assays performed on the sample with the information entered into the laboratory information system based on the patient-identifying indicia of the receptacle.

18. The method of claim 8, wherein the patient-identifying indicia of the receptacle are machine-readable, and wherein the automatically determining step comprises using the patient-identifying indicia as a reference point for locating the plurality of discrete areas of the receptacle.

19. The method of claim 1, wherein the receptacle is a tube or vial.

20. The method of claim 19, wherein the sample is obtained from an animal, environmental, food, industrial, or non-environmental water source.

21. The method of claim 20, wherein the sample is obtained from an animal source, and wherein the sample is selected from the group consisting of peripheral blood, plasma, serum, bone marrow, urine, bile, mucus, phlegm, saliva, cerebrospinal fluid, stool, biopsy tissue including lymph nodes, respiratory tissue or exudates, gastrointestinal tissue, cervical swab sample, and semen.

22. A method of processing a sample in a receptacle having one or more assay order states, the method comprising the steps of:

collecting the sample within the receptacle, wherein the receptacle comprises a label, and wherein the label comprises:

a plurality of discrete areas having known associations with multiple assays, each of the plurality of discrete areas having a known association with one assay of the multiple assays, and each of the plurality of discrete areas being configured to be altered from a first assay order state to a second assay order state, wherein for each of the plurality of discrete areas:

the first assay order state is defined by an undeformed protuberance in the discrete area, the first assay order state indicating that the one assay having the known association with the discrete area is not to be performed, the second assay order state is defined by the presence of a deformed protuberance in the discrete area, the second assay order state indicating that the one assay having the known association with the discrete area is to be performed, a plurality of assay-identifying indicia, each assay-identifying indicia indicating the one assay having the known association with of the corresponding discrete area of the plurality of discrete areas, and each assay-identifying indicia including alphanumeric characters or graphical symbols, and patient-identifying indicia; and altering at least one discrete area of the plurality of discrete areas from the first assay order state to the second assay order state by applying pressure to the at least one discrete area such that an associated protuberance is deformed.

23. The method of claim 22, further comprising the steps of:

automatically determining assay order states of the plurality of discrete areas by determining which of the plurality of discrete areas has been altered from the first assay order state to the second assay order state; and performing the one assay associated with each of the plurality of discrete areas determined to have the second assay order state.

24. The method of claim 23, wherein the automatically determining step comprises using a reader of an automatic sample processing instrument.

25. The method of claim 23, wherein the automatically determining step comprises using a hand-held reader operatively coupled to an automatic sample processing instrument.

26. The method of claim 23, further comprising the step of receiving a form comprising patient-identifying indicia having a known association with the patient-identifying indicia of the receptacle.

27. The method of claim 26, wherein the patient-identifying indicia of the form comprise a first barcode, and wherein the patient-identifying indicia of the receptacle comprise a second barcode.

28. The method of claim 27, wherein the first barcode and the second barcode are identical.

29. The method of claim 26, further comprising the step of entering information on the form into a laboratory information system.

30. The method of claim 29, wherein the entering step is automatic.

31. The method of claim 29, wherein the entering step occurs concurrently with or after the performing step.

32. The method of claim 29, further comprising the step of associating results of each of the multiple assays performed on the sample with the information entered into the laboratory information system based on the patient-identifying indicia of the receptacle.

33. The method of claim 23, wherein the patient-identifying indicia of the receptacle are machine-readable, and wherein the automatically determining step comprises using the patient-identifying indicia as a reference point for locating the plurality of discrete areas of the receptacle.

34. The method of claim 22, wherein the multiple assays determine the presence or absence of different analytes in the sample.

35. The method of claim 22, wherein the patient-identifying indicia of the receptacle are machine-readable.

36. The method of claim 22, wherein the patient-identifying indicia of the receptacle comprise a unique serial number.

37. The method of claim 22, wherein the plurality of discrete areas and the plurality of assay-identifying indicia are arranged in a series of rows and columns on the label.

38. The method of claim 37, wherein each of the plurality of discrete areas and the corresponding assay-identifying indicia are located in the same row.

39. The method of claim 22, wherein the receptacle is a tube or vial.

40. The method of claim 39, wherein the sample is obtained from an animal, environmental, food, industrial, or non-environmental water source.

41. The method of claim 40, wherein the sample is obtained from an animal source, and wherein the sample is selected from the group consisting of peripheral blood, plasma, serum, bone marrow, urine, bile, mucus, phlegm, saliva, cerebrospinal fluid, stool, biopsy tissue including lymph nodes, respiratory tissue or exudates, gastrointestinal tissue, cervical swab sample, and semen.

* * * * *

UNITED STATES PATENT AND TRADEMARK OFFICE
CERTIFICATE OF CORRECTION

| | | |
|---|---|---|
| PATENT NO. | : 12,320,818 B2 | Page 1 of 1 |
| APPLICATION NO. | : 16/499814 | |
| DATED | : June 3, 2025 | |
| INVENTOR(S) | : Rolf Silbert | |

It is certified that error appears in the above-identified patent and that said Letters Patent is hereby corrected as shown below:

In the Specification

In Column 4, Line 29, delete "operational" and insert -- operation --, therefor.

In Column 11, Line 60, delete "user" and insert -- use --, therefor.

In Column 12, Line 2, delete "area of areas" and insert -- areas --, therefor.

In Column 15, Line 6, delete "envelop," and insert -- envelope, --, therefor.

In the Claims

In Column 22, Line 49, in Claim 22, delete "of the" and insert -- the --, therefor.

Signed and Sealed this
Twenty-third Day of September, 2025

John A. Squires
*Director of the United States Patent and Trademark Office*